US005770597A

United States Patent [19]
Kim et al.

[11] Patent Number: 5,770,597
[45] Date of Patent: Jun. 23, 1998

[54] QUINOLONE DERIVATIVES AND PROCESSES FOR PREPARING THE SAME

[75] Inventors: Wan Joo Kim; Tae Ho Park; Moon Hwan Kim; Bong Jin Kim, all of Daejeon, Rep. of Korea; Neil D. Pearson, Surrey, England

[73] Assignees: Korea Research Institute of Chemical Technology, Daejeon, Rep. of Korea; Smithkline Beecham P.L.C., Brentford, United Kingdom

[21] Appl. No.: 492,086

[22] PCT Filed: Jan. 18, 1994

[86] PCT No.: PCT/KR94/00005

§ 371 Date: Oct. 11, 1995

§ 102(e) Date: Oct. 11, 1995

[87] PCT Pub. No.: WO94/15938

PCT Pub. Date: Jul. 21, 1994

[30] Foreign Application Priority Data

Jan. 18, 1993 [KR] Rep. of Korea ........................... 93-543

[51] Int. Cl.$^6$ ........................ A61K 31/47; C07D 215/56
[52] U.S. Cl. ..................................... 514/230.2; 514/231.5; 514/294; 514/300; 544/32; 544/101; 546/94; 546/113; 546/123
[58] Field of Search .............................. 546/94, 113, 123; 544/32, 101; 514/230.2, 231.5, 294, 300

[56] References Cited

U.S. PATENT DOCUMENTS

| | | | |
|---|---|---|---|
| 4,954,507 | 9/1990 | Weber et al. | 514/300 |
| 4,965,273 | 10/1990 | Weber et al. | 514/300 |
| 4,990,517 | 2/1991 | Petersen et al. | 514/300 |
| 5,059,597 | 10/1991 | Petersen et al. | 514/224 |
| 5,091,384 | 2/1992 | Kim et al. | 514/215 |
| 5,140,033 | 8/1992 | Schriewer et al. | 514/312 |
| 5,202,337 | 4/1993 | Petersen et al. | 514/312 |
| 5,245,037 | 9/1993 | Kuramoto et al. | 546/156 |
| 5,498,615 | 3/1996 | Kim et al. | 514/300 |

FOREIGN PATENT DOCUMENTS

| | | |
|---|---|---|
| 3514076 | 10/1985 | Germany . |
| 3632222 | 7/1988 | Germany . |

OTHER PUBLICATIONS

Bay Y3118, a Novel 4–Quinolone Synthesis and In Vitro Activity, U. Petersen et al., 32$^{nd}$ ICAAC (Proceeding No. 642, 1992) (Paper and Abstract 642).

Primary Examiner—Bernard Dentz
Attorney, Agent, or Firm—Baker & Botts, L.L.P.

[57] ABSTRACT

The present invention relates to quinoline derivatives substituted in the 7-position by a trans-2,8-diazabicyclo[4.3.0] nonan-8-yl group having a broad antibacterial spectrum and to processes for preparing the same.

5 Claims, No Drawings

QUINOLONE DERIVATIVES AND PROCESSES FOR PREPARING THE SAME

This application is a 371 of PCT/KR94/00005 filed Jan. 18, 1994.

TECHNICAL FIELD

The present invention relates to novel quinolone derivatives which have a broad antibacterial spectrum, and processes for preparing the same.

BACKGROUND ART

Nalidixic acid developed in 1963 is the first one of quinolonecarboxylic acid-type antibacterials. Quinolonecarboxylic acid-type antibacterials are known to exhibit strong antibacterial activity against aerobic *Gram-negative* bacteria and have been effectively used as a treatment for urethritis. Among these quinolone carboxylic acid-type antibacterials, especially norfloxacin, ciprofloxacin, of loxacin, etc. are clinically used. However, these prior art compounds suffer from the disadvantage that they have drastically inferior antibacterial activity against *Gram-positive* bacteria, while they have superior antibacterial activity against *Gram-negative* bacteria. Especially, these quinolone-type antibacterials are known to have weak antibacterial activity against *Gram-positive* bacteria such as *Staphylococcus* or *Enterococcus* which show high resistance to sepem-type or β-lactam-type antibacterial agents.

DISCLOSURE OF INVENTION

The present invention provides novel quinolone derivatives of formula (I), (III) and (IV) below and processes for preparing the same.

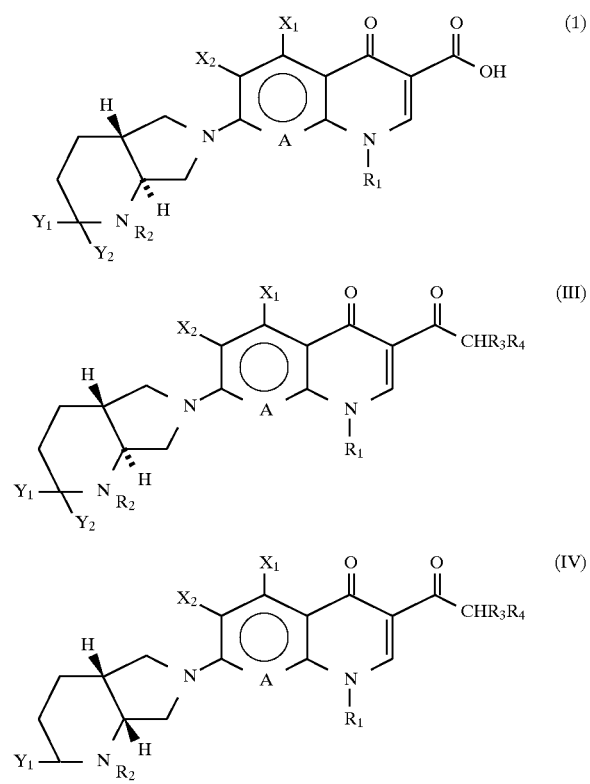

wherein, $X_1$ represents hydrogen, amino group, halogen such as chloro, fluoro, or lower alkyl such as methyl;

$X_2$ represents hydrogen or halogen;

$Y_1$ and $Y_2$ each represents hydrogen, or lower alkyl ($C_{1-3}$) group;

$R_1$ represents a straight chain or cyclic lower alkyl group having 1 to 3 carbon atoms or a straight chain or cyclic lower alkyl group having 1 to 3 carbon atoms which is substituted with a halogen atom, a phenyl group or a phenyl group substituted with one or two halogen atoms;

$R_2$ represents hydrogen, or lower alkyl such as methyl, ethyl;

$R_3$ and $R_4$ each represent hydrogen, nitro group, methoxycarbonyl group, ethoxycarbonyl group or nitryl group; and A represents nitrogen atom or

in which Y represents hydrogen, halogen, lower alkyl or alkoxy or together with $R_1$ forms —$CH_2CH_2CH_2$—, —$CH_2CH_2CH(CH_3)$—, —$OCH_2CH_2$—, —$OCH_2CH(CH_3)$—, —$SCH,CH_2$—, or —$SCH_2CH(CH_3)$—.

A is preferably nitrogen, methyn, fluoromethyn, chloromethyn, methoxymethyn, or methylmethyn.

Lower alkyl is preferably $C_{1-6}$ alkyl, more preferably $C_{1-4}$ alkyl, such as methyl or ethyl. $X_2$ halogen is preferably fluorine.

$R_1$ is preferably ethyl, cyclopropyl, halogen (F, Cl)-substituted cyclopropyl or halogen substituted phenyl.

The present invention is described in detail hereinbelow.

The present invention provides novel quinolone carboxylic acid derivatives of formula (I), and specifically, to novel quinolone carboxylic acid derivatives of formula (I) below which have trans-2,8-diazabicyclo[4.3.0]nonane derivatives represented by the formula (II) at 7-position of quinolone nucleus and possess a broad spectrum of potent antibacterial activities, and to processes for preparing the same.

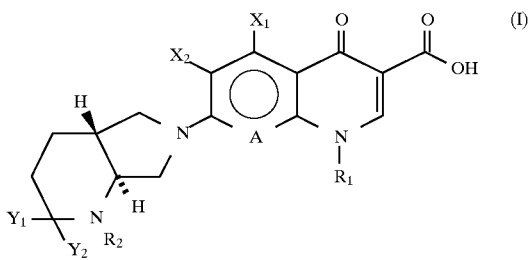

wherein, $X_1, X_2, Y_1, Y_2, R_1, R_2$, and A are the same as defined above.

The present invention also provides novel quinolone carboxylic acid derivatives represented by the formula (III) and (IV) including mixtures thereof which show a broad spectrum of potent antibacterial activities, and to processes for preparing the same.

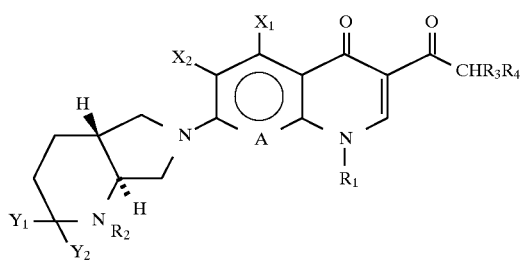

(III)

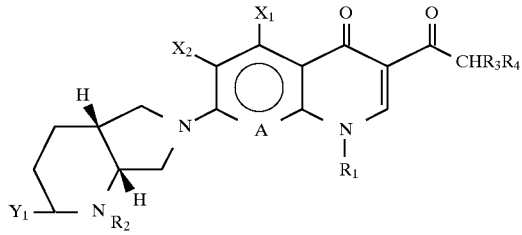

(IV)

wherein,
$X_1, X_2, Y_1, Y_2, R_1, R_2, R_3, R_4$, and A are the same as defined above.

The present invention provides trans-2,8-diazabicyclo[4.3.0]nonane derivatives represented by the formula (II) which are used as a side chain at 7-position of novel quinolone carboxylic acid derivatives (I) and processes for preparing the same.

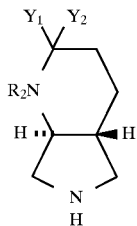

(II)

wherein,
$Y_1, Y_2$, and $R_2$ are the same as defined above.

The present invention also provides novel processes for preparing cis-2,8-diazabicyclo[4.3.0]nonane derivatives represented by the following formula (V) which are used as a side chain at 7-position of formula (IV) above.

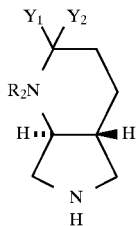

(V)

wherein,
$Y_1$ and $R_2$ are the same as defined above.

Quinolone derivatives of formula (I) according to the present invention may be prepared by condensing optionally protected trans-2,8-diazabicyclo [4.3.0]nonane derivatives of formula (II) above with the known compound of formula (VI-1) (P. D. Fernandes, "International Telesymposium on Quinolone", J. R. Prous Science, Barcelona, Spain, 1989. 1–143) in a solvent, in the presence of an inorganic or organic base, as described in the process (A). Inorganic bases used in this process include potassium carbonate and the like. Organic base used herein include diazabicyclo[5.4.0]undecene (DBU), pyridine, triethylamine and the like.

The above reaction may be carried out at a temperature between room temperature and 150° C. The reaction time is about 1 to 10 hours.

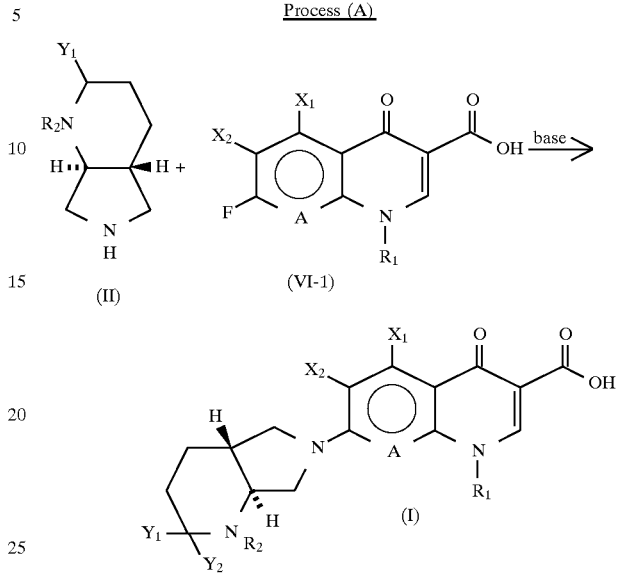

Process (A)

wherein,
$X_1, X_2, Y_1, Y_2, R_1, R_2$, and A are the same as defined above or $R_2$ is a protecting group such as t-butoxy carbonyl which is removed subsequently.

Also, quinolone derivatives represented by formula (III) of the present invention may be prepared by the following process (B). That is, the compound of formula (III) can be prepared by stirring compound of formula (I) and an activating agent such as carbodiimidazole (CDI) under reflux in the presence of a solvent such as chloroform, tetrahydrofuran (THF) and the like and then stirring nitromethane, diethylmalonate, dimethylmalonate, ethylnitrylacetate under reflux together with solution treated with a base such as sodium hydride, calcium carbonate, sodium carbonate in the presence of a solvent such as THF, and the like.

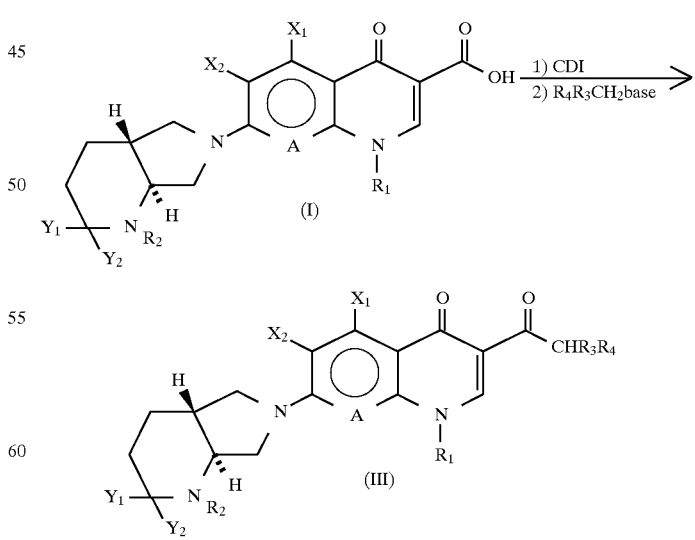

Process (B)

wherein,
$X_1, X_2, Y_1, Y_2, R_1, R_2, R_3$, and $R_4$ are the same as defined above; and represent nitro group, nitryl group, diethoxycarbonyl group, or dimethoxycarbonyl group, and thereafter optionally interconverting $R_3$ and $R_4$.

Quinolone derivatives represented by formula (IV) of the present invention may be prepared by the following process (C). That is, the compound of formula (IV) can be prepared by reacting optionally protected cis-2,8-diazabicyclo[4.3.0] nonane derivatives of formula (V) with the compound of formula (IV-2) under reflux stirring in a solvent of acetonitrile or dimethylformamide (DMF) in the presence of basic, neutral, or acidic alumina.

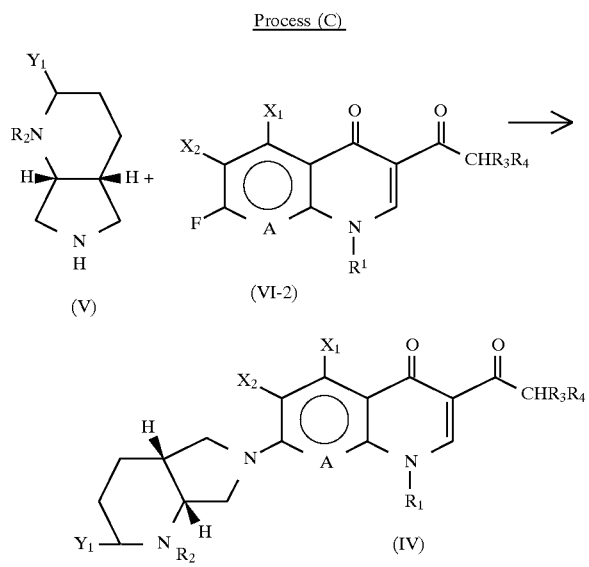

wherein,
$X_1$, $X_2$, $Y_1$, $R_1$, $R_2$, $R_3$, and A are the same as defined above or $R_2$ is a protecting group such as t-butoxy carbonyl which is removed subsequently.

Novel quinolone derivatives of formula (IV) above can be also prepared by stirring the condensed compound with the solution under reflux. The condensed compound may be prepared by reacting cis-2,8-diazabicyclo[4.3.0]nonane derivatives of formula (V) with the known compound of formula (VI-2) in a solvent in the presence of an organic or inorganic base. Organic base used herein include diazabicyclo[5.4.0]undecene(DBU), pyridine, triethylamine and the like. Inorganic bases used in this process include potassium carbonate and the like. The above reaction may be carried out at a temperature between room temperature and 150° C. The reaction time is about 1 to 10 hours. The above solution is prepared by stirring carbodiimidazole under reflux in a solvent such as chloroform, tetrahydrofuran, and then stirring nitromethane, diethylmalonate, dimethylmalonate, ethylnitrylacetate under reflux with a base such as sodium hydride, calcium carbonate, sodium carbonate in a solvent such as tetrahydrofuran and the like.

The compounds of formula (I), (III) and (IV) above can be converted to the pharmaceutically acceptable salts thereof according to the conventional method. For example, these compounds can be converted to salts of inorganic acid such as hydrochloric acid, sulfuric acid, and phosphoric acid or salts of organic acid such as methansulfonic acid, lactic acid, oxalic acid, and acetic acid.

Trans-2,8-diazabicyclo[4.3.0]nonane derivatives of the following formula (II) according to the present invention can be prepared by the following Process (D). The Process(D) comprises the following four steps:

Step (1)

The compound of formula (VIII) can be prepared by reacting the known compound of formula (VII) (J.Org.Chem. 48, 1129 (1983)) with β-alanine derivatives in the presence of ethanol under reflux;

Step (2)

The compound of formula (IX) can be prepared by cyclizating the compound of formula (VIII) with alkoxide such as sodium ethoxide or potassium t-butoxide at room temperature in the aromatic solvent such as benzene, toluene;

Step (3)

The compound of formula (X) can be prepared by reacting the carbonyl compound of formula (IX) with tosylhydrazine in a solvent of ethanol or methanol to obtain tosylhydrazone and then, by reducing the resulting compound with sodium shanobrohydride; and Step (4)

The compound of formula (II) can be prepared by debenzylating the compound of formula (X) in methanol solvent in the presence of a catalyst of palladium or platinum.

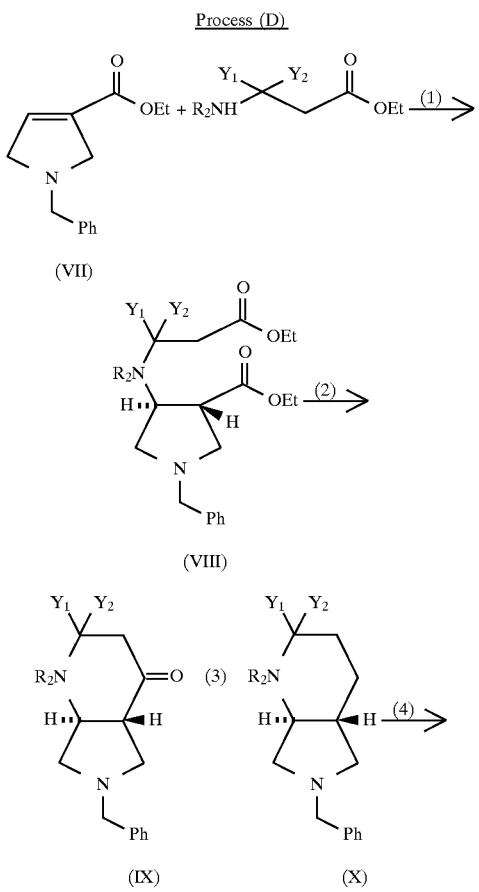

Process (D)

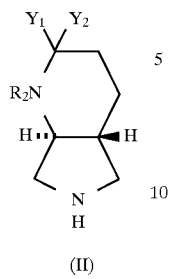

wherein, $Y_1$, $Y_2$, and $R_2$ are the same as defined above.

Trans-2,8-diazabicyclo[4.3.0]nonane derivatives of the following formula (II) according to the present invention can also be prepared by the following Process (E). The Process (E) comprises the following seven steps:

Step (5)

Trans isomer of formula (XIII) can be prepared by reacting the known compound of formula (XII) (UK Patent No. 1,086,637, or Chemical Abstract, 68, 96695W) with β-alanine derivatives in the presence of ethanol under reflux;

Step (6)

Cis isomer of formula (XIV) can be prepared by reacting trans isomer of formula (XIII) with methansulfonyl chloride or lithium chloride, in methylene chloride or chloroform, in the presence of an organic base such as triethylamine or diisopropylethylamine, at the temperature between 0° C. and 60° C.;

Step (7)

Trans isomer of formula (XV) can be prepared by reacting cis isomer of formula (XIV) with potassium cyanate or sodium cyanate in DMF solvent;

Steps (8) and (9)

The compound of formula (IX) can be prepared from the compound of formula (XV) by the same method as Step (2) of Process (D) above;

Step (10)

The compound of formula (X) can be prepared by reducing the compound of formula (IX) with zinc amalgam in the presence of hydrochloric acid; and Step (11)

The compound of formula (II) can be prepared from the compound of formula (X) by the same method as Step (4) of Process (D) above.

Process (E)

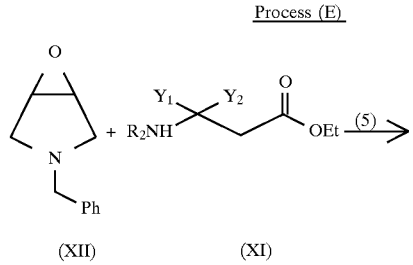

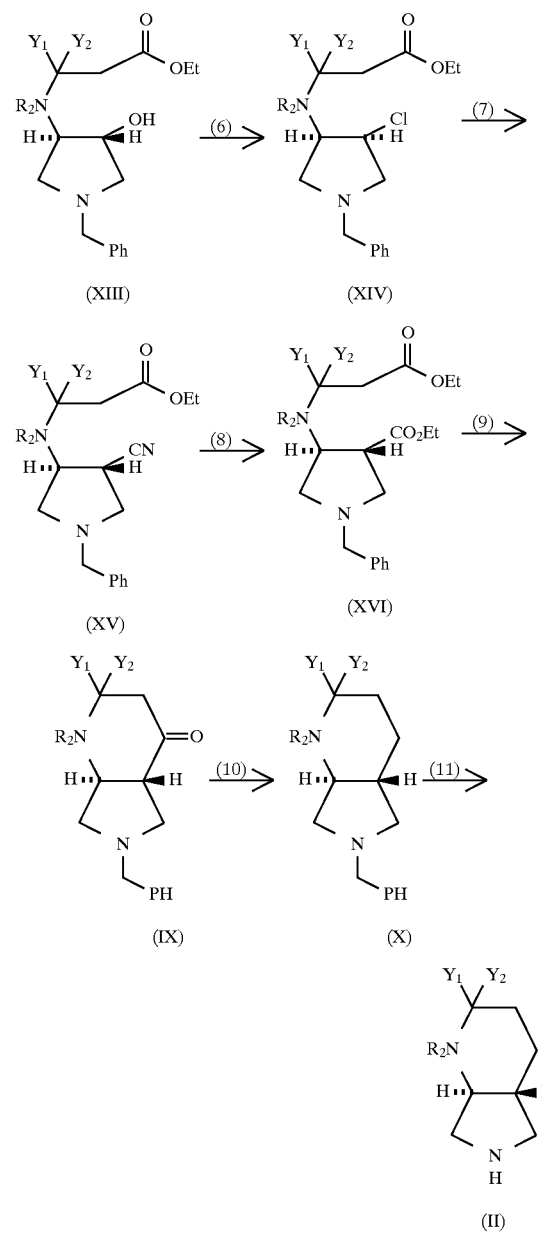

wherein, $Y_1$, $Y_2$ and $R_2$ are the same as defined above.

Cis-2,8-diazabicyclo[4.3.0]nonane derivatives of the formula (V) according to the present invention can be prepared by the following Process (F). The Process(D) comprises the following seven steps:

Step (12)

The ester compound of formula (XVIII) can be prepared by suspending conventional pyridine derivatives of formula (XVII) in methanol and adding thionylchloride thereto and then stirring the resulting compound under reflux;

Step (13)

Alcohols of formula (XIX) can be prepared by reducing the compound of formula (XVIII) with lithium aluminum hydride in ethylether or THF;

Step (14)

The compound of formula (XX) can be prepared by chlorinating, brominating, or methane sulfonylating alcohols of formula (XIX);

Step (15)

The cyclized compound of formula (XXI) can be prepared by reacting the compound of formula (XX) with tocylimide and sodiumhydride in DMF;

Step (16)

Amines of formula (XXII) can be prepared by hydrolyzing the compound of formula (XXI) with 48% of hydrobromic acid;

Step (17)

Salts of pyridine of formula (XXIII) can be prepared by reacting amine compounds of formula (XXII) with methaneiodide and acid anhydrous in a solvent of methylene chloride or ethyl alcohol; and Step (18)

Cis-2,8-diazabicyclo[4.3.0]nonane derivatives of formula (V) can be prepared by hydrogenating the compound of formula (XXIII) in a solvent of methanol or ethanol in the presence of a catalyst of palladium or platinum.

ii) Preparation of trans-N,N'-dibenzyl-2,8-diazabicyclo[4.3.0]-5-oxononane 20.5 g of trans-1-benzyl-3-carboethoxy-4-[N-benzyl-N(2carboethoxy) ethyl]aminopyrrolidine was dissolved in 200 ml of toluene and the reaction mixture was cooled in ice bath and then 6.1 g of potassium t-buthoxide was added dropwise thereto. After adding dropwise, the reaction mixture was heated to 40° C. and stirred for 4 hours. The reaction mixture was evaporated under reduced pressure and the residue was dissolved in water. The resulting product was neutralized with aqueous solution of sodium bicarbonate, extracted with ethylacetate and then dried with anhydrous magnesium sulfate. The solvent was evaporated under reduced pressure and then the residual product was purified by a silica gel column chromatography to give 11.8 g of the above title compound (yield: 71%).

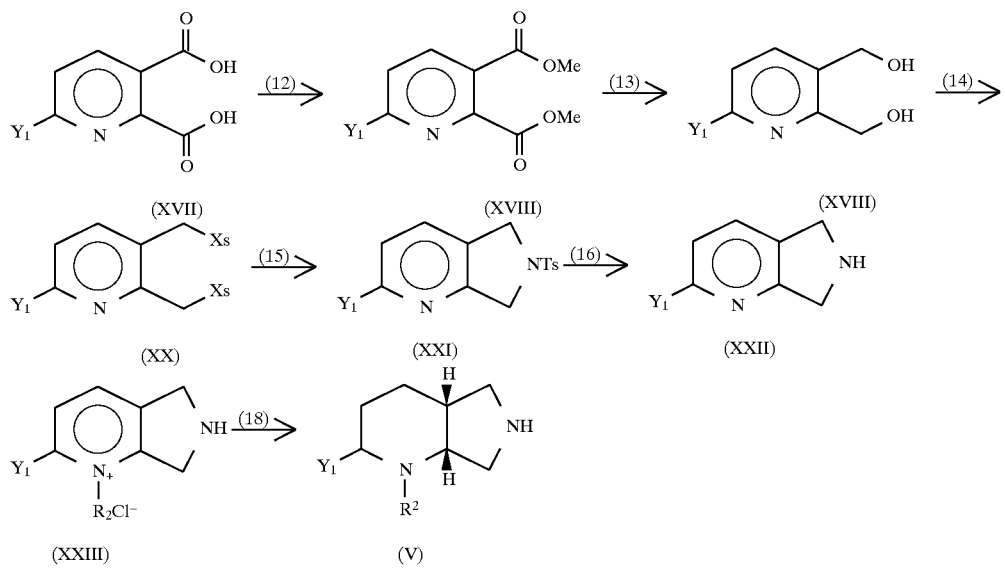

wherein,

X₃ represents chloro, bromo, or methanesulfonyloxy group; and

Y₁ and R₂ are the same as defined above.

The following examples are intended to further illustrate the present invention, without limiting the scope of the invention.

EXAMPLE 1

Preparation of trans-piperidinopyrrolidine

1) Preparation according to Process (D)

i) Preparation of trans-1-benzyl-3-carboethoxy-4-[N-benzyl-N-(2-carboethoxy)ethyl]aminopyrrolidine A mixture of 23.9 g of 1-benzyl-3-ethoxycarbonyl-3-pyrroline and 19.2 g of β-N-benzylalanine ethylester were added to 100 ml of ethanol and stirred under reflux for 3 days. The solvent was evaporated under reduced pressure and then the residual product was purified by a silica gel column chromatography (nucleic acid-ethylacetate (3:1)) to give 26.9 g of the above title compound (yield: 65%).

$^{1}$H-NMR(CDCl$_3$, δ): 2.21(2H, m), 2.51(2H, m), 3.10–4.01(6H, m), 3.71(6H, s),7.25(10H, m)

$^{1}$H-NMR(CDCl$_3$, δ): 2.30–3.0(9H, m), 3.20–3.70(2H, q), 3.50(6H, s), 3.4(1H, q), 7.15(10H, m)

iii) Preparation of trans-N,N'-dibenzylpiperidinopyrrolidine 15.9 g of trans-N,N'-dibenzyl-2,8-diazabicyclo[4.3.0]-5-oxononane and 9.3 g of tosyl hydrazine was added to 100 ml of ethanol and then dehydrated with Dean-Stark distillation apparatus. 14 g of sodium borohydride was added thereto and the mixture was stirred for 4 hours. The solvent was evaporated under reduced pressure and then the residue was extracted with ethylether. The mixture of ethylether was evaporated under reduced pressure and then the residual product was purified by a silica gel column chromatography (nucleic acid-ethylacetate (3:1)) to give 13.2 g of the above title compound (yield: 87%).

$^{1}$H-NMR(CDCl$_3$, δ): 1.54–2.01(5H, m), 2.74–3.10(7H, m), 3.20–3.70(4H, m) 7.30(10H, m)

iv) Preparation of trans-piperidinopyrrolidine dihydrochloride 13.15 g of trans-N,N'-dibenzylpiperidinopyrrolidine were dissolved in 50 ml of methanol and then 1.0 g of 10% Pd/C and 60 ml of 30% methanol were added thereto. The resulting solution was hydrogenated by Parr hydrogenation reactor and debenzylated. The reaction mixture was filtered through celite and the filtrate was evaporated under reduced pressure. The residue was dissolved in 10 ml of methanol and ethylether was added dropwise to the mixture. The resulting mixture was solidified and filtered to give 7.43 g of the above title compound (yield: 93%).

$^1$H-NMR(CDCl$_3$, δ): 1.50–190(5H, m), 2.74–3.01(7H, m)

2) Preparation according to Process (E)

i) Preparation of trans-1-benzyl-3-hydroxy-4-[N-benzyl-N-(2-carboethoxy)ethyl]aminopyrrolidine 87.25 g (0.5 mol) of 3-benzyl-6-oxy-3-azabicyclo[3.1.0] nucleic acid and 113.8 g (0.51 mol) of 3N-benzylaminopropanoate were put into 200 ml of pyridine and stirred under reflux for 3 days. The reaction mixture was evaporated under reduced pressure to remove pyridine and then the residue was subjected to a silica gel column chromatography (nucleic acid-ethylacetate (1:1)) to give 166.2 g of the above title compound (yield: 87%).

$^1$H-NMR(CDCl$_3$, δ): 1.26(3H, t), 2.24(2H, m), 2.50(2H, m), 3.90(1H, m), 3.10–4.0(9H, m), 4.20(2H, q), 7.23(10H, m)

ii) Preparation of cis-1-benzyl-3-chloro-4-[N-benzyl-N-(2-carboethoxy)ethyl]aminopyrrolidine 95.5 g (0.25 mol) of trans-1-benzyl-3-hydroxy-4-[N-benzyl-N-(2-carboethoxy) ethyl]aminopyrrolidine and 70 ml of triethylamine were dissolved in 11 of methylene chloride and 31.4 g of methane sulfonyl chloride were added dropwise thereto at 0° C. 21.3 g of anhydrous lithium chloride were added to the mixture and the reaction mixture was heated to 60° C. and stirred for 20 hours. The reaction mixture was cooled, washed with water and dried over anhydrous magnesium sulfate. After the solvent was evaporated under reduced pressure, the residue was purified by a silica gel column chromatography (nucleic acid-ethylacetate (3:1)) to give 80.15 g of the above title compound (yield: 82%).

$^1$H-NMR(CDCl$_3$, δ): 1.26(3H, t), 2.24–2.52(4H, m), 3.10–4.0(9H, m), 4.14(1H,m),4.20(2H, q), 7.30(10H, m)

iii) Preparation of trans-1-benzyl-3-cyano,-4-[N-benzyl-N-(2-carboethoxy)ethyl]aminopyrrolidine 40.1 g (0.1 mol) of trans-1-benzyl-3-chloro-4-[N-benzyl-N-(2-carboethoxy)ethyl]aminopyrrolidine and 7.8 g of potassium cyanate were put into 100 ml of DMF and the mixture was heated at 60° C. for 14 hours while stirring. The reaction mixture was added to 400 ml of ice water while stirring and the produced solid was filtered. The resulting solid was dissolved in ethylacetate and then the mixture was subjected to a silica gel column chromatography (nucleic acid-ethylacetate (3:1)) to give 30.5 g of the desired compound (yield: 78%).

$^1$H-NMR(CDCl$_3$, δ): 1.27(3H, t), 2.24(2H, m), 2.50(2H, m), 3.10–4.0(9H,m),4.20(2H, q), 7.30(10 H, m)

iv) Preparation of trans-1-benzyl-3-carboethoxy-4-[N-benzyl-N-(2-carboethoxy)ethyl]aminopyrrolidine 30.0 g of trans-1-benzyl-3-cyano-4-[N-benzyl-N-(2-carboethoxy)ethyl]aminopyrrolidine were put into 300 ml of 10% hydrochloric acid and the mixture was refluxed for 6 hours. After water was evaporated under reduced pressure, the residue was heated and dried in vacuum drier for 10 hours. The residue was suspended in 200 ml of methanol and 30 ml of thionylchloride was added dropwise to the mixture while refluxing and further refluxed for 5 hours. The reaction mixture was evaporated under reduced pressure, the residue was put into methanol and 11 g of sodium methoxide was added gradually thereto at 0° C. The resulting mixture was evaporated under reduced pressure again, dissolved in ethylacetate and washed with water. The organic layer was dried over anhydrous magnesium sulfate and evaporated under reduced pressure, and the residue was subjected to a silica gel column chromatography (nucleic acid-ethylacetate (3:1)) to give 30.5 g of the title compound (yield: 61%).

$^1$H-NMR(CDCl$_3$, δ): 2.21(2H, in), 2.51(2H, m), 3.10–4.01(6H, m), 3.71(6H, s),7.25(1OH, m)

v) Preparation of trans-N,N'-dibenzyl-2,8-diazabicyclo[4.3.0]-5-oxononane 20.5 g of trans-1-benzyl-3-carboethoxy-4-[N-benzyl-N-(carboethoxy)ethyl]aminopyrrolidine was dissolved in 200 ml of toluene and the reaction mixture was cooled in ice bath and then 6.1 g of potassium t-buthoxide was added dropwise thereto. After adding dropwise, the reaction mixture was heated to 40° C. and stirred for 4 hours. The reaction mixture was evaporated under reduced pressure and the residue was dissolved in water. The resulting product was neutralized with aqueous solution of sodium bicarbonate, extracted with ethylacetate and then dried over anhydrous magnesium sulfate. The solvent was evaporated under reduced pressure and then the residual product was purified by a silica gel column chromatography to give 11.8 g of the above title compound (yield: 74%).

$^1$H-NMR(CDCl$_3$, δ): 2.30–3.0(9H, m), 3.20–3.70(2H, q), 3.50(6H, s), 3.4(1H, q),7.15(10H, m)

vi) Preparation of trans-N, N'-dibenzyl-piperidinopyrrolidine 6.5 g of zinc powder were put into 15 ml of aqueous solution of 5% HgCl$_2$ and the mixture solution was shaken for 1 hour. The supernatant was removed and 9.6 g of N,N'-dibenzyl-2,8-diazabicyclo[4.3.0]-5-oxononane was added thereto. 10 ml of 15% hydrochloric acid was added and the solution was heated while refluxing for 6 hours. While refluxing, 10 ml of 5% hydrochloric acid was added several times. The mixture was cooled and 40 ml of ethylacetate was added thereto and then supernatant of the mixture was removed. The suspension was filtered and the filtrate was neutralized with 5% KOH and extracted with ethylacetate. The extracted solution was dried over anhydrous magnesium sulfate. The solvent was evaporated under reduced pressure and then the residual product was purified by a silica gel column chromatography (nucleic acid-ethylacetate (3:1)) to give 7.44 g of the above title compound (yield: 81%).

$^1$H-NMR(CDCl$_3$, δ): 1.54–2.01(5H, m), 2.74–3.10(7H, m), 3.2–3.70(4H, m),7.30(10H, m)

vii) Preparation of trans-piperidinopyrrolidine dihydrochloride 6.12 g (0.02 mol) of trans-N,N'-dibenzyl-piperidinopyrrolidine were dissolved in 30 ml of methanol and then 0.5 g of 10% Pd/C and 5 ml of fumaric acid were added thereto. The resulting solution was hydrogenated by Parr hydrogenation reactor (initial hydrogen pressure: 60 psi) to debenzylate. The reaction mixture was filtered through celite and the filtrate was evaporated under reduced pressure. The residue was dissolved in 10 ml of 30% hydrochloride methanol and ethylether was added dropwise to the mixture. The resulting mixture was solidified and filtered to give 3.62 g of the above title compound (yield: 92%).

$^1$H-NMR(CDCl$_3$, δ): 1.50–1.90(5H, m), 2.74–3.01(7H, m)

EXAMPLE 2

Preparation of trans-3-methyl-piperidinopyrrolidine dihydrochloride

According to the same method as i), ii), iii), iv), v), vi) and vii) of Process (E) in Example 1, 121 g of methyl-3-(N-benzyl)aminobutanoate as a starting material was used to give 22.9 g of the above title compound (total yield: 10.1%).

$^1$H-NMR(CDCl$_3$, δ): 1.42–1.90(7H, m), 2.74–3.01(7H, m)

EXAMPLE 3

Preparation of cis-piperidinopyrrolidine dihydrobromide

1) Preparation of 2,3-dimethoxycarboylpyridine 26.7 g of 2,3-pyridinedicarboxylic acid were put into 500 ml of methanol saturated with hydrogen chloride and the mixture was refluxed for 10 hours. Methanol was evaporated under reduced pressure and then the residual product was purified by a silica gel column chromatography (nucleic acid-ethylacetate (1:1)) to give 25.1 g of the above pure title compound (yield: 85%).

$^1$H-NMR(CDCl$_3$, δ): 3.95(6H, s), 7.34(1H, m), 7.51(1H, d), 8.84(1H, d)

2) Preparation of 2,3-dihydroxymethylpyridine

A solution prepared by dissolving 29.5 g, of 2,3-dimethoxycarbonylpyridine in 200 ml of ethylether was added dropwise to a solution prepared by suspending 10 g of lithium aluminum hydride in 300 ml of dried ethylether at 0° C. This mixed solution was stirred at 20° C. for 3 hours and 30 ml of water was slowly added thereto at 0° C. The resulting solution was stirred for 5 hours at the room temperature and solid was filtered through celite. The filtrate was evaporated under reduced pressure and then the residual product was purified by a silica gel column chromatography (chloroform : methanol (10:1)) to give 10.4 g of the above title compound (yield: 75%).

$^1$H-NMR(CDCl$_3$+DMSO-d$_6$, δ): 4.58(2H, d), 4.67(2H, d), 5.13(1H, s), 5.30(1H, s), 7.34(1H, m), 7.45(1H, d), 8.45(1H, d)

3) Preparation of 2,3-dichloromethylpyridine hydrochloride 13.9 g of 2,3-dihydroxymethylpyridine and thionylchloride were evaporated under reduced pressure to give 21.2 g of the above title compound in yellow solid (yield: 99%).

$^1$H-NMR(CDCl$_3$+DMSO-d$_6$, δ): 5.10(2H, s), 5.15(2H, s), 7.81(1H, m), 8.15(1H, m), 8.15(1H, d), 8.95(1H, d)

4) Preparation of 2,3-dihydro-2-p-toluene sulfonyl-1H-pyrrolo[2.3.c]pyridine

A solution prepared by suspending 0.9 g of 60% sodium-hydride in 50 ml of dried dimethylformamide was slowly added dropwise over 2 hours to a solution prepared by dissolving 3.5 g of p-toluenephosphenylamide in 20 ml of dried dimethylformamide. The reacting mixture was stirred for 1 hour at the room temperature and then stirred again for 1 hour at the temperature between 65 and 70° C. A solution prepared by dissolving 2.13 g of 2,3-dichloromethylpyridine in 3 ml of dried dimethylformamide was added to the reaction mixture. The resulting mixture was stirred for 3 hours at the same temperature and 20 ml of water was added thereto. The solvent was evaporated off under reduced pressure. 20 ml of water was added again to the mixture, and the resulting mixture was saturated with sodium hydroxide and extracted with 100 ml of ethylacetate. The extracted solution was dried over anhydrous magnesium sulfate. The solvent was evaporated under reduced pressure and then the residual product was purified by a silica gel column chromatography (nucleic acid-ethylacetate (1:2)) to give 1.8 g of the above title compound (yield: 65%).

$^1$H-NMR(CDCl$_3$, δ): 2.45(3H, s), 4.65–4.68(4H, d), 7.15(1H, m), 7.35(3H, d,d), 7.81(2H, m), 8.46(1H, d)

5) Preparation of 2,3-dihydro-1H-pyrrolo[2.3.c]pyridine dihydrobromide 74 g of 2,3-dihydro-2-p-toluene sulfonyl-1H-pyrrolo[2.3.c.]pyridine was put into 20 ml of 48% hydrobromide, and 1.75 g of phenol and 9.18 ml of propionic acid was added thereto and then the reaction mixture was refluxed for 48 hours. The reaction mixture was evaporated under reduced pressure and 30 ml of water was added to. The water layer was washed with ethylacetate and then water soluble layer was concentrated and stood in a refrigerator to give 2.23 g of the above title compound (yield: 79%).

$^1$-NMR(DMSO-d$_6$, δ): 5.24(4H, δ), 7.85(1H, m), 8.20(1H, d), 8.90(1H, d)

6) Preparation of cis-piperidinopyrrolidine dihydrobromide 1.42 g of 2,3-dihydro-1H-pyrrolo[2.3.c]pyridinehydrobromide was dissolved in 30 ml of methanol and the mixture was suspended with 1 g of 10% Pd/C. The resulting solution was hydrogenated by Parr hydrogenation reactor (initial hydrogen pressure: 60 psi) to debenzylate. After the reaction was finished, the reaction solution was filtered through celite and the solvent was evaporated in vacuo to give 1.42 g of the above title compound (yield: 99%).

$^1$H-NMR(DMSO-d$_6$, δ): 1.51–1.94(5H, m), 2.71–3.12(7H, m)

EXAMPLE 4

Preparation of cis-3-methyl-piperidinopyrrolidine dihydrobromide

According to the same method as i), ii), iii), iv), v) and vi) of Example 3, 28.1 g of 5-methyl-2,3-dicarboxypyridine was used to give 8.88 g of the above title compound (total yield: 30%).

$^1$H-NMR(DMSO-d$_6$, δ): 1.2(4H, m), 1.50–1.91(5H, m), 2.74–3.01(7H, m), 4.10(1H, m), 7.7(1H, dxd), 8.6(1H, s)

EXAMPLE 5

Preparation of 1-cyclopropyl-6-fluoro-7-[(trans-piperidinopyrrolidine)-8-yl]-8-chloro-1,4-dihydroguinoline-4-oxo-3-carboxylicacid 300 mg of 1-cyclopropyl-6,7-difluoro-1,4-dihydroquinoline-4-oxo-3-carboxylic acid and 210 mg of trans-piperidinopyrrolidine dihydrochloride were suspended in 10 ml of anhydrous acetonitrile and 0.18 ml of DBU was added thereto. The reaction mixture was refluxed for 6 hours and cooled to the room temperature. The produced solid was filtered and washed with acetonitrile to give 405.5 mg of the above title compound (yield: 100%).

$^1$H-NMR(DMSO-$d_6$, δ): 1.22(4H, m), 1.61–2.01(5H, m), 2.74–3.01(7H, m), 4.08(1H, m), 7.56(1H, dxd), 8.61(1H, s)

EXAMPLE 6

Preparation of 1-cyclopropyl-6.8-difluoro-7-[(trans-piperidinopyrrolidine)-8-yl]-1,4-dihydroquinoline-4-oxo-3-carboxylic acid 283 mg of 1-cyclopropyl-6,7,8-trifluoro-1,4-dihydroquinoline-4-oxo-3-carboxylic acid and 210 mg of trans-piperidinopyrrolidine dihydrochloride were treated according to the same method as that of Example 5 to give 327 mg of the above title compound (yield: 84%).

$^1$H-NMR(DMSO-$d_6$, δ): 1.2(4H, m), 1.50–1.91(5H, m), 2.74–3.01(7H, m), 4.10(1H, m), 7.7(1H, dxd), 8.6(1H, s)

Following compounds may be prepared by the process similar to that described in Example 5.

1-cyclopropyl-6-fluoro-7-[(trans-piperidinopyrrolidine)-8-yl]-1,4dihydroquinoline-4-oxo-3-carboxylic acid;

1-cyclopropyl-5-amino-6,8-difluoro-7-[(trans-piperidinopyrrolidine)-8-yl]-1,4-dihydroquinoline-4-oxo-3-carboxylic acid;

1-cyclopropyl-5-methyl-6-fluoro-7-[(trans-piperidinopyrrolidine)-8-yl]-1,4-dihydroquinoline-4-oxo-3-carboxylic acid;

1-cyclopropyl-6-fluoro-7-[(trans-piperidinopyrrlidine)-8-yl]-8-methoxy-1,4-dihydroquinoline-4-oxo-3-carboxylic acid;

1-cyclopropyl-6-fluoro-7-[(trans-piperidinopyrrolidine)-8-yl]-1,4-dihydro-4-oxo-1,8-naphthyridin-3-carboxylic acid;

1-(2,4-difluorophenyl)-6-fluoro-7-[(trans-piperidinopyrrolidine)-8-yl]- 1,4-dihydro-4-oxo-1,8-naphthyridin-3-carboxylic acid;

9-fluoro- 10-[(trans-piperidinopyrrolidine)-8-yl]-2,3-dihydro-3-methyl-7-oxo-7H-pyrido[1,2,3-de][1,4]-benzooxazine-6-carboxylic acid;

1-cyclopropyl-6,8-difluoro-7-[(3-methyl-2,8-diazabicyclo[4.3.0]nonane)-8-yl]-1,4-dihydroquinoline-4-oxo-3-carboxylic acid;

1-cyclopropyl-6-fluoro-7-[(trans-3-methyl-2,8-diazabicyclo[4.3.0]nonane)-8-yl]-8-chloro-1,4-dihydroquinoline-4-oxo-3-carboxylic acid;

1-cyclopropyl-5-amino-6,8-difluoro-7-[(trans-3-methyl-2,8-diazabicyclo[4.3.0]nonane)-8-yl]-8-methoxy-1,4-dihydroguinoline-4-oxo-3-carboxylic acid;

1-cyclopropyl-5-methyl-6-fluoro-7-[(trans-3-methyl-2,8-diazabicyclo[4.3.0]nonane)-8-yl]-1,4-dihydroquinoline-4-oxo-3-carboxylic acid;

1-cyclopropyl-6-fluoro-7-[(trans-3-methyl-2,8-diazabicyclo[4.3.0]nonane)-8-yl]-8-methoxy-1,4-dihydroquinoline-4-oxo-3-carboxylic acid;

1 -cyclopropyl-6-fluoro-7-[(trans-3-methyl-2,8-diazabicyclo[4.3.0]nonane)-8-yl]-1,4-dihydro-4-oxo-1,8-naphthyridin-3-carboxylic acid; and 9-fluoro-10-[(trans-3-methyl-2,8-diazabicyclo[4.3.0]nonane)-8-yl]-2,3-dihydro-3-methyl-7-oxo-7H-pyrido[1,2,3-de][1,4]-benzooxazine-6-carboxylic acid.

EXAMPLE 7

Preparation of 1-cyclopropyl-3-nitroacetyl-6-fluoro-8-chloro-7-[(trans-piperidinopyrrolidine)-8-yl]-4-oxo-1,4-dihydroquinoline hydrochloride 183 mg of nitromethane was dissolved in 10 ml of tetrahydrofuran and 120 mg of 60% NaH was suspended in the mixture. The resulting solution was stirred for 3 hours at 40° C. 403.5 mg of 1-cyclopropyl-6-fluoro-8-chloro-7-[(trans-2-(N-t-butoxycarbonyl)piperidinopyrrolidine)-8-yl]-oxo- 1,4-dihydroquinoline-3-carboxylic acid, 324 mg of CDI and 10 ml of chloroform were put into the above solution. The resulting solution was stirred under reflux for 12 hours and the solvent was evaporated under reduced pressure. The produced residue was added to 10 ml of THF and the mixture was stirred under reflux for 4 hours. The reaction solvent was evaporated under reduced pressure and the residue was suspended in 20 ml of water. The suspension was neutralized with acetic acid and extracted with ethylacetate (20 ml ×3). The extracted solution was dried over anhydrous magnesium sulfate and the solvent was evaporated under reduced pressure. The produced residue was purified by column chromatography ($CHCl_3$: MeOH=9 : 1) to give 389 mg of 1-cyclopropyl-3-nitroacetyl-6-fluoro-8-chloro-7-[(trans-2-(N-t-butoxycarbonyl)piperidinopyrrolidine)-8-yl]-4-oxo-1,4-dihydroquinoline. This compound was put into 5 ml of 10% methanol solution of hydrogen chloride and the mixture was stirred for 4 hours at room temperature and then 5 ml of ethylether was added thereto. The produced solid was filtered and dried under reduced pressure to give 335 mg of the above title compound (yield: 64%).

$^1$H-NMR(DMSO-$d_6$, δ): 1.22(4H, m), 1.01–1.98(5H, m), 2.78–3.08(7H, m), 4.06(1H, m), 6.18(2H, s), 7.74(1H, dxd), 8.78(1H, s)

EXAMPLE 8

Preparation of 1-cyclopropyl-3-nitroacetyl-6-fluoro-8-methoxy-7-[(trans-piperidinopyrrolidine)-8-yl]-4-oxo-1,4-dihydroquinoline hydrochloride 497 mg of 1-cyclopropyl-6-fluoro-8-methoxy-7-[(trans-2-(N-t-butoxy carbonyl)piperidinopyrrolidine)-8-yl]-oxo-1,4-dihydroquinoline-3-carboxylic acid were treated according to the same method as that of Example 7 to give 327 mg of the title compound (yield: 74%).

$^1$H-NMR(DMSO-$d_6$, δ): 1.20(4H, m), 1.51–1.91(5H, m), 2.70–3.04(7H, m), 3.86(3H, s), 4.00(1H, m), 6.16(2H, s), 7.86(1H, d), 8.84(1H, s)

Following compounds may be prepared by the process similar to that described in Example 7.

1-cyclopropyl-3-nitroacetyl-6,8-difluoro-7-[(trans-piperidinopyrrolidine)-8-yl]-4-oxo-1,4-dihydroquinoline hydrochloride;

1-cyclopropyl-3-nitroacetyl-5-amino-6,8-difluoro-7-[(trans-piperidinopyrrolidine)-8-yl]-4-oxo-1,4-dihydroquinoline hydrochloride;

1-(2,4-difluoro)phenyl-3-nitroacetyl-6-fluoro-7-[(trans-piperidinopyrrolidine)-8-yl]-4-oxo-1,4-dihydro- 1,8-naphthyridine hydrochloride;

1-cyclopropyl-3-nitroacetyl-6,8-difluoro-7-[(trans-2,8-diazabicyclo[4.3.0]nonane-3-methyl)-8-yl]-4-oxo-1,4-dihydroquinoline hydrochloride; and 1-cyclopropyl-3-(diethoxycarbonyl)acetyl-6,8-difluoro-7-[(trans-piperidinopyrrolidine)-8-yl]-4-oxo-1,4-dihydroquinoline hydrochloride.

1-cyclopropyl-3-(dimethoxycarbonyl)acetyl-6-fluoro-8-methoxy-7-[(trans-piperidinopyrrolidine)-8-yl]-4-oxo-1, 4-dihydroquinoline hydrochloride.

EXAMPLE 9

Preparation of 1-cyclopropyl-3-nitroacetyl-6-fluoro-8-methoxy-7-[(cis-piperidinopyrrolidine)-8-yl]-4-oxo-1,4-dihydroquinoline hydrochloride 1) Preparation according to Process (B)

497 mg of 1-cyclopropyl-6-fluoro-8-methoxy-7-[(cis-2-(N-t-butoxycarbonyl) piperidinopyrrolidine)-8-yl]-4-oxo-1,4-dihydroquinoline-3-carboxylic acid were treated according to the same method as that of Example 7 to give 314 mg of the above title compound (yield: 71%).

$^1$H-NMR(DMSO-d$_6$, δ): 1.18(4H, m), 1.57–2.00(5H, m), 2.70–3.04(7H, m), 3.86(3H, s), 4.00(1H, m), 6.18(2H, s), 7.86(1H, d), 8.84(1H, s)

2) Preparation according to Process (C)

i) Preparation of 1-cyclopropyl-3-nitroacetyl-6,7-difluoro-8-methoxy-4-oxo-1,4-dihydroquinoline 566 mg of 1-cyclopropyl-6,7,8-trifluoro-4-oxo-1,4-dihydroquinoline-3-carboxylic acid and 648 mg of CDI were put into 20 ml of THF and the mixture solution is stirred under reflux for 24 hours (A solution). 366 mg of nitromethane was mixed in 5 ml of THF and 240 mg of 60% NaH added thereto. The mixture solution was stirred for 24 hours at room temperature and the above A solution was added thereto. The resulting solution was stirred under reflux for 14 hours. The reaction mixture was cooled and the solvent was evaporated under reduced pressure. The produced residue was purified by column chromatography (nucleic acid: ethylacetate =5 : 1) to give 450 mg of the above title compound (yield: 69%).

$^1$H-NMR(DMSO-d$_6$, δ): 1.20(4H, m), 3.62(3H, s), 4.00(1H, m), 6.12(2H, s), 7.67(1H, d), 8.60(1H, s)

ii) Preparation of 1-cyclopropyl-3-nitroacetyl-6-fluoro-8-methoxy-7-[(cis-piperidinopyrrolidine)-8-yl]-4-oxo-1,4-dihydroquinolinehydrochloride 338 mg of 1-cyclopropyl-3-nitroacetyl-6,7-difluoro-8-methoxy-4-oxo-1,4-dihydroquinoline and 310 mg of cis-piperidinopyrrolidine were dissolved in 10 ml of acetonitrile. 310 mg of alumina were added thereto and the mixture was stirred for 10 hours at 60° C. The reaction mixture was evaporated under reduced pressure and the produced residue was suspended in methanol and the mixture solution was stirred under reflux and filtered. The filtrate was collected and evaporated under reduced pressure. The produced residue was put into 15 ml of 10% solution of HCl-methanol and the mixture solution was stirred for 2 hours at room temperature. 15 ml of ethylether was added thereto and the resulting solution was filtered to give 296 mg of the above title compound (yield: 67%).

$^1$H-NMR(DMSO-d$_6$, δ): 1.18(4H, m), 1.57–2.00(5H, m), 2.70–3.04(7H, m), 3.86(3H, s), 4.00(1H, m), 6.18(2H, s), 7.86(1H, d), 8.84(1H, s)

Following compounds may be prepared by the process similar to that described in Example 9.

1-cyclopropyl-3-(diethoxycarbonyl)acetyl-6-fluoro-8-chloro-7-[(cis-piperidinopyrrolidine)-8-yl]-4-oxo-1,4-dihydroquinoline hydrochloride;

1-cyclopropyl-3-nitroacetyl-6,8-difluoro-7-[(cis-2,8-diazabicyclo[4.3.0]nonane-3-methyl)-8-yl]-4-oxo-1,4-dihydroquinoline hydrochloride; and 1-cyclopropyl-3-(dimethoxycarbonyl)acetyl-6-fluoro-8-methoxy-7-[(cis-piperidinopyrrolidine)-8-yl]-4-oxo-1,4-dihydroquinoline hydrochloride.

COMPARATIVE EXAMPLE 1

Preparation of 1-cyclopropyl-6-fluoro-8-methoxv-7-[(cis-piperidinopyrrolidine)-8-yl]-4-oxo-1,4-dihydroquinoline-3-carboxylic acid 295 mg of 1-cyclopropyl-6,7-difluoro-8-methoxy-1,4-dihydro-4-oxo-3-carboxylic acid and 210 mg of cis-piperidinopyrrolidine dihydrochloride were treated according to the same method as that of Example 5 to give 324 mg of the above title compound (yield: 81%).

$^1$H-NMR(CDCl$_3$, δ): 1.14–1.22(4H, m), 1.51–1.91(5H, m), 2.71–2.98(7H, m), 3.82(3H, s), 4.00(1H, m), 7.84(1H, d), 8.80(1H, s)

COMPARATIVE EXAMPLE 2

Preparation of 1-cyclopropyl-6.8-difluoro-7-[(cis-piperidinopyrrolidine-3-methyl)-8-yl]-4-oxo-1,4-dihydroquinoline-3-carboxylic acid 283 mg of 1-cyclopropyl-6,7,8-trifluoro-1,4-dihydroquinoline-4-oxo-3-carboxylic acid and 232 mg of cis-3-methylpiperidinopyrrolidine dihydrochloride were treated according to the same method as that of Example 5 to give 280 mg of the above title compound (yield: 71%).

$^1$H-NMR(CDCl$_3$, δ): 1.20(4H, m), 1.56–1.92(8H, m), 2.70–3.00(6H, m), 4.00(1H, m), 7.72(1H, d), 8.68(1H, s)

In vitro antibacterial activity test

The results of in vitro antibacterial activity test are shown in Tables 1 and 2. The numbers in Tables represent the minimal inhibitory concentration (MIC, μg/ml) of the corresponding strains and MIC was determined in accordance with the agar culture medium two-fold dilution method by using a Mueller-Hinton agar.

Hoechst standard strains were used. The strains having $10^7$ CFU/ml were inoculated on the culture medium, and the growth of the strains was observed after incubating them at 37° C. for 18 hours, in which ciprofloxacin was used as a control.

TABLE 1

In vitro antibacterial activity test (MIC, ug/ml)

| Strain | A | B | C | D | Cipro-floxacin |
|---|---|---|---|---|---|
| Streptococcus pyogenes 308A | 0.391 | 0.781 | 0.781 | 1.563 | 3.125 |
| Streptococcus pyogenes 77A | 0.098 | 0.195 | 0.391 | 0.391 | 0.781 |
| Streptococcus faecium MD 8b | 0.098 | 0.195 | 0.391 | 0.391 | 0.781 |
| Staphylococcus aureus SG 511 | 0.025 | 0.098 | 0.098 | 0.195 | 0.195 |
| Staphylococcus aureus 285 | 0.025 | 0.098 | 0.025 | 0.391 | 0.391 |
| Staphylococcus aureus 503 | 0.025 | 0.195 | 0.025 | 0.391 | 0.781 |
| Escherichia coli O 78 | <0.002 | <0.025 | <0.002 | 0.049 | <0.002 |
| Escherichia coil DC 0 | 0.195 | 0.391 | 0.195 | 0.195 | 0.195 |
| Escherichia coil DC 2 | 0.013 | 0.098 | 0.098 | 0.098 | 0.098 |
| Escherichia coil TEM | 0.007 | 0.049 | 0.004 | 0.098 | 0.007 |
| Escherichia coil 1507E | 0.025 | 0.049 | 0.025 | 0.098 | 0.007 |

TABLE 1-continued

In vitro antibacterial activity test (MIC, ug/ml)

| Strain | A | B | C | D | Cipro-floxacin |
|---|---|---|---|---|---|
| *Pseudomonas aeruginosa* 9027 | 0.781 | 0.781 | 0.781 | 1.563 | 0.391 |
| *Pseudomonas aeruginosa* 1592E | 0.781 | 0.781 | 0.781 | 0.781 | 0.195 |
| *Pseudomonas aeruginosa* 1771 | 0.781 | 1.563 | 0.781 | 0.781 | 0.195 |
| *Pseudomonas aeruginosa* 1771M | 0.195 | 0.391 | 0.391 | 0.391 | 0.049 |
| *Salmonella typhimurium* | <0.002 | 0.049 | 0.007 | 0.098 | 0.007 |
| *Klebsiella aerogenes* 1082E | <0.002 | 0.098 | 0.049 | 0.049 | <0.002 |
| *Klebsiella aerogenes* 1552E | 0.049 | 0.098 | 0.013 | 0.049 | 0.013 |
| *Enterobacter cloacae* P 99 | 0.004 | 0.025 | 0.004 | 0.013 | 0.007 |
| *Enterobacter cloacae* 1321E | <0.002 | 0.013 | <0.002 | 0.013 | <0.002 |

A: The compound of Example 5
B: The compound of Example 7
C: The compound of Example 8
D: The compound of Example 9

What is claimed is:

1. A trans-racemic mixture of a quinolone of Formula (I):

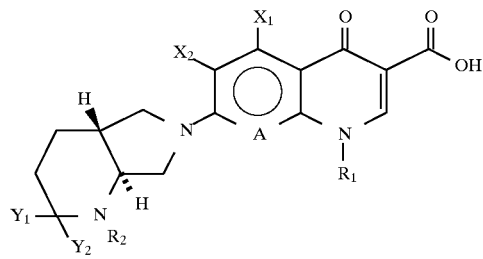

wherein,

X$_1$ represents hydrogen, amino, halogen, or lower alkyl;
X$_2$ represents hydrogen or halogen;
Y$_1$ and Y$_2$ each represents hydrogen, or lower alkyl (C$_{1-3}$) group;
R$_1$ represents a straight chain or cyclic lower alkyl group having 1 to 3 carbon atoms or a straight chain or cyclic lower alkyl group having 1 to 3 carbon atoms which is substituted with a halogen atom, a phenyl group or a phenyl group substituted with one or two halogen atoms;
R$_2$ represents hydrogen, or lower alkyl: and
A represents nitrogen atom or

in which Y represents hydrogen, halogen, lower alkyl or alkoxy or together with R$_1$ forms —CH$_2$CH$_2$CH$_2$—, —CH$_2$CH$_2$CH(CH$_3$)—, —OCH$_2$CH$_2$—, —OCH$_2$CH(CH$_3$)—, —SCH$_2$CH$_2$—, or —SCH$_2$CH(CH$_3$)—.

2. A trans-racemic mixture of claim 1 of Formula (I) selected from the group consisting of;

1-cyclopropyl-6-fluoro-7-[(trans-piperidinopyrrolidine)-8-yl]-8-chloro-1,4-dihydroquinoline-4-oxo-3-carboxylic acid, 1-cyclopropyl-6,8-difluoro-7-[(trans-piperidinopyrrolidine)-8-yl]-1,4-dihydroquinoline-4-oxo-3-carboxylic acid, 1-cyclopropyl-6-fluoro-7-[(trans-piperidinopyrrolidine)-8-yl]-1,4-dihydroquinoline-4-oxo-3-carboxylic acid, 1-cyclopropyl-5-amino-6,8-difluoro-7-[(trans-piperidinopyrrolidine)-8-yl]-1,4-dihydroquinoline-4-oxo-3-carboxylic acid, 1-cyclopropyl-5-methyl-6-fluoro-7-[(trans-piperidinopyrrolidine)-8-yl]1,4-dihydroquinoline-4-oxo-3-carboxylic acid, 1-cyclopropyl-6-fluoro-7-[(trans-piperidinopyrrolidine)-8-yl]-8-methoxy-1,4-dihydroquinoline-4-oxo-3-carboxylic acid, 1-cyclopropyl-6-fluoro-7-[(trans-piperidinopyrrolidine)-8-yl]- 1,4-dihydro-4-oxo-1,8-naphthyridin-3-carboxylic acid, 1-(2,4-difluorophenyl)-6-fluoro-7-[(trans-piperidinopyrrolidine)-8-yl]-1,4-dihydro-4-oxo-1,8-naphthyridin-3-carboxylic acid, 9-fluoro-10-[(trans-piperidinopyrrolidine)-8-yl]-2,3-dihydro-3-methyl-7-oxo-7H-pyrido[1,2,3-de][1,4]-benzooxazine-6-carboxylic acid, 1-cyclopropyl-6,8-difluoro-7-[(trans-3-methyl-2,8-diazabicyclo[4.3.0]nonane)-8-yl]-1,4-dihydroquinoline-4-oxo-3-carboxylic acid, 1-cyclopropyl-6-fluoro-7-[(trans-3-methyl-2,8-diazabicyclo[4.3.0]nonane)-8-yl]-8-chloro-1,4-dihydroquinoline-4-oxo-3-carboxylic acid, 1-cyclopropyl-5-amino-6,8-difluoro-7-[(trans-3-methyl-2,8-diazabicyclo[4.3.0]nonane)-8-yl]-1,4-dihydroquinoline-4-oxo-3-carboxylic acid, 1-cyclopropyl-5-methyl-6-fluoro-7-[(trans-3-methyl-2,8-diazabicyclo[4.3.0]nonane)-8-yl]-1,4-dihydroquinoline-4-oxo-3-carboxylic acid, 1-cyclopropyl-6-fluoro-7-[(trans-3-methyl-2,8-diazabicyclo[4.3.0]nonane)-8-yl]-8-methoxy-1,4-dihydroquinoline-4-oxo-3-carboxylic acid, 1-cyclopropyl-6-fluoro-7-[(trans-3-methyl-2,8-diazabicyclo[4.3.0)]nonane)-8-yl]-1,4-dihydro-4-oxo-1,8-naphthyridin-3-carboxylic acid, 9-fluoro-10-[(trans-3-methyl-2,8-diazabicyclo[4.3.0]nonane)-8-yl]-2,3-dihydro-3-methyl-7-oxo-7H-pyrido[1,2,3-de][1,4]-benzooxazine-6-carboxylic acid.

3. A process for preparing a trans-racemic mixture of Formula (I) of claim 1 comprising condensing optionally protected trans-2,8-diazabicyclo [4.3.0]nonane derivatives of formula (II) with the compound of formula (VI-1) in a solvent, in the presence of an inorganic base such as calcium carbonate and the like or an organic base such as diazabicyclo[5.4.0]undecene (DBU), pyridine, triethylamine and the like:

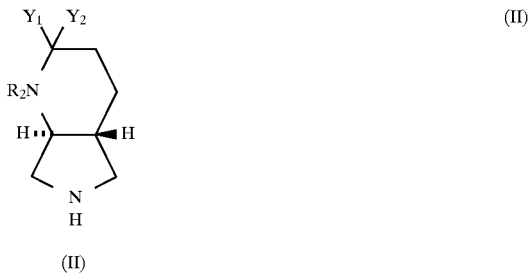

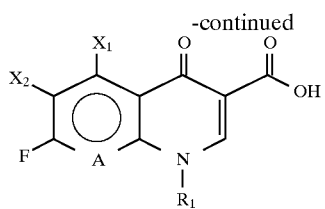

wherein,

X₁, X₂, Y₁, Y₂, R₁, R₂, and A are the same as defined in claim 1 or R₂ is a protecting group, and thereafter optionally deprotecting.

4. A pharmaceutical composition which contains a trans-racemic mixture or pharmaceutically acceptable salt thereof Formula (I) according to claim 1, as an active ingredient in an effective amount.

5. A method for the treatment of bacterial infection characterized in that a pharmaceutical composition comprising a trans-racemic mixture or pharmaceutically acceptable salt thereof according to Formula (I) is administered to a host in need of such treatment in the therapeutically effective amount.

* * * * *

UNITED STATES PATENT AND TRADEMARK OFFICE
CERTIFICATE OF CORRECTION

PATENT NO. : 5,770,597
DATED : June 23, 1998
INVENTOR(S) : Wan Joo Kim et al.

It is certified that error appears in the above-identified patent and that said Letters Patent is hereby corrected as shown below:

Title page,
Item [57], ABSTRACT,
Line 1, "quinoline" should read -- quinolone --.

Column 1,
Line 19, "of loxacin" should read -- ofloxacin --.

Column 3,
Line 46, (formula V): "$Y_1 Y_2$" should read -- $Y_1$ --

Columns 9 and 10,
After formula (XXII) and before formula (XXIII), insert the following

Column 14,
Line 29, "$^1$-NMR(dmso-d$_6$, δ):" should read -- $^1$H-NMR(dmso-d$_6$, δ): --.
Line 61, "dihydroguinoline" should read -- dihydroquinoline --.

Column 15,
Line 47, "-8-yl]-8-methoxy-1,4-" should read -- -8-yl]-1,4 --.
Line 48, "dihydroguinoline" should read -- dihydroquinoline --.

Column 18, Table I,
Lines 60-65, each instance "coil" should read -- coli --.

Column 22,
Lines 8 and 9, "thereof Formula (I)" should read -- thereof : Formula (I) --.

Column 19, claim 2,
Line 60, "mixture of claim 1 of Formula (I)" should read -- mixture of Formula (I) of claim 1 --.

UNITED STATES PATENT AND TRADEMARK OFFICE
CERTIFICATE OF CORRECTION

PATENT NO.    : 5,770,597
DATED         : June 23, 1998
INVENTOR(S)   : Wan Joo Kim et al.

It is certified that error appears in the above-identified patent and that said Letters Patent is hereby corrected as shown below:

Column 20, claim 3,
Lines 47 and 48, "mixture of claim 1 of Formula (I)" should read -- mixture of Formula (I) of claim 1 --.

Column 22, claim 5,
Line 15, "Formula (I)" should read -- Formula (I) of claim 1 --.

Signed and Sealed this

Eleventh Day of December, 2001

*Attest:*

*Attesting Officer*

NICHOLAS P. GODICI
*Acting Director of the United States Patent and Trademark Office*

UNITED STATES PATENT AND TRADEMARK OFFICE
Certificate

Patent No. 5,770,597                                                                                 Patented: June 23, 1998

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Wan Joo Kim; Tae Ho Park; Moon Hwan Kim; and Bong Jin Kim, all of Daejeon, Republic of Korea.

Signed and Sealed this Thirtieth Day of April 2002.

*JOHN KIGHT III*
*Supervisory Patent Examiner*
*Art Unit 1612*